United States Patent
Hughes

(10) Patent No.: US 9,864,888 B2
(45) Date of Patent: Jan. 9, 2018

(54) HISTOLOGICAL SAMPLE TRACKING SYSTEM

(71) Applicants: PYRAMID INNOVATION, Netherfield Sussex (GB); Thomas Fergus Hughes, Netherfield Sussex (GB)

(72) Inventor: Thomas Fergus Hughes, Netherfield (GB)

(73) Assignee: PYRAMID INNOVATION, Netherfield, Sussex (GB)

( * ) Notice: Subject to any disclaimer, the term of this patent is extended or adjusted under 35 U.S.C. 154(b) by 87 days.

(21) Appl. No.: 14/909,403

(22) PCT Filed: Aug. 5, 2014

(86) PCT No.: PCT/GB2014/052394
§ 371 (c)(1),
(2) Date: Feb. 1, 2016

(87) PCT Pub. No.: WO2015/019073
PCT Pub. Date: Feb. 12, 2015

(65) Prior Publication Data
US 2016/0180134 A1    Jun. 23, 2016

(30) Foreign Application Priority Data

Aug. 7, 2013  (GB) .................................. 1314103.1

(51) Int. Cl.
*G06F 19/00* (2011.01)
*G06K 7/14* (2006.01)
(Continued)

(52) U.S. Cl.
CPC ......... *G06K 7/1413* (2013.01); *G06F 19/366* (2013.01); *G06K 7/10554* (2013.01);
(Continued)

(58) Field of Classification Search
CPC ... G06Q 10/087; G06F 19/366; G06F 19/327; G06F 19/3412; G06K 7/1413; G06K 7/10554
(Continued)

(56) References Cited

U.S. PATENT DOCUMENTS 6,141,602 A    10/2000 Igarashi et al.
2007/0141711 A1    6/2007 Stephens et al.
(Continued)

FOREIGN PATENT DOCUMENTS

CN    202584129 U    12/2012
EP    1 936 539 A1    6/2008
(Continued)

OTHER PUBLICATIONS

PCT/GB2014/052394 International Search Report and Written Opinion.
GB 1314103.1 Search Report under Section 17.

*Primary Examiner* — Laura Gudorf
(74) *Attorney, Agent, or Firm* — Fay Sharpe LLP

(57) ABSTRACT

There is provided a histological sample tracking system, comprising a plurality of tracking stations (TS1, TS2) and controllers (CNT_I, CNT_R1, CNT_R2), each tracking station incorporating a scanner (SCN1, SCN2) and one of the controllers (CNT_R1, CNT_R2). The scanner (SCN_1, SCN_2) is configured to scan identifiers of carriers of histological samples, and the controller (CNT_R1, CNT_R2) is configured to receive the identifiers and send messages based on the identifiers to other ones of the controllers (CNT_I, CNT_R1, CNT_R2). The controllers together form a private network, wherein one of the controllers is assigned as an interface controller (CNT_I) and the remaining controllers are assigned as remote controllers (CNT_R1, CNT_R2). The controller assigned as the interface controller (CNT_I) allows access to an external net-
(Continued)

Figure 1:
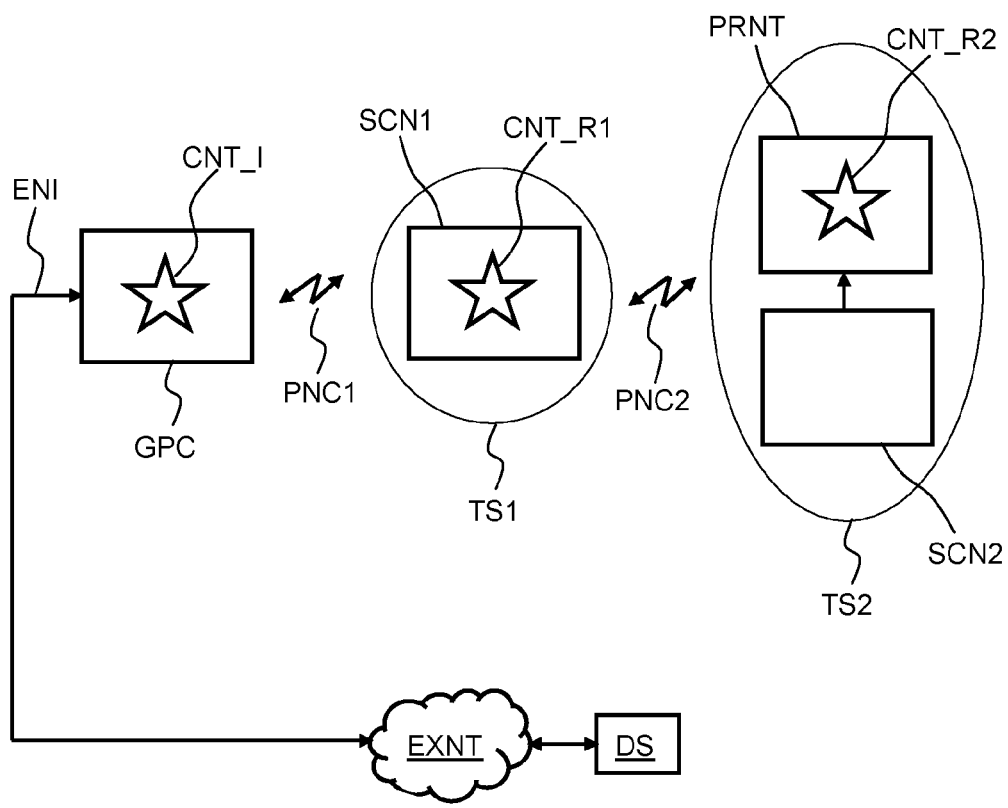

work (EXNT), and the controllers assigned as remote controllers (CNT_R1, CNT_R2) refuse all access requests from any external networks.

20 Claims, 3 Drawing Sheets

(51) Int. Cl.
  *G06K 7/10* (2006.01)
  *G06Q 10/08* (2012.01)
(52) U.S. Cl.
  CPC ......... *G06Q 10/087* (2013.01); *G06F 19/327* (2013.01); *G06F 19/3412* (2013.01)
(58) Field of Classification Search
  USPC ........................................................ 235/385
  See application file for complete search history.

(56) References Cited

U.S. PATENT DOCUMENTS

| | | | |
|---|---|---|---|
| 2009/0048870 | A1 | 2/2009 | Godshall et al. |
| 2011/0225286 | A1* | 9/2011 | Francis ............... H04L 63/0272 709/224 |
| 2012/0124157 | A1* | 5/2012 | Marriott ................ G06F 3/1423 709/208 |
| 2014/0040193 | A1* | 2/2014 | McLean ................ G06Q 40/04 707/610 |

FOREIGN PATENT DOCUMENTS

| | | |
|---|---|---|
| WO | WO/2001/020532 A1 | 3/2001 |
| WO | WO 2003/021525 A2 | 3/2003 |
| WO | WO 2008/123499 A1 | 10/2008 |
| WO | WO 2008/156566 A1 | 12/2008 |
| WO | WO 2010/151761 | 12/2010 |

\* cited by examiner

HISTOLOGICAL SAMPLE TRACKING SYSTEM

The present invention relates to a histological sample tracking system, for example for use within laboratories where various steps during histological sample processing are required to be carried out at different locations.

There are several devices used within laboratories for printing or marking laboratory sample containers and holders such as microscope slides, tissue processing cassettes, sample pots, vials etc. They have also enabled laboratories to print barcodes directly onto the sample carriers, which can be read by barcode scanners to reduce the risk of errors due to misreading and human error.

The introduction of barcodes has made it possible to machine read the barcodes on sample carriers and to produce computer based tracking software for tracking the various steps that take place during histological sample processing. These systems run on computers that are typically networked together. The laboratory would typically have computers located at various locations within the laboratory, and each computer would typically have a barcode reader attached to scan sample carriers to record their location and time. Locations where sample carriers are printed or marked are also provided with a printer attached to the computer. One example of such a histological sample tracking system is described in WO 2010/151761.

The problem with such systems is that computers take up valuable space, are vulnerable to misuse, virus attack, require maintenance, multiple cables and other devices connected to them in order to provide the desired function.

It is therefore an aim of the invention to provide an improved system for tracking histological samples.

According to a first aspect of the invention, there is provided a histological sample tracking system, comprising a plurality of tracking stations and controllers, each tracking station incorporating a scanner and one of the controllers. The scanner is configured to scan identifiers of carriers of histological samples, and the controller is configured to receive the identifiers and send messages based on the identifiers to other ones of the controller. The controllers together form a private network, wherein one of the controllers is assigned as an interface controller and the remaining controllers are assigned as remote controllers. The controller assigned as the interface controller allows access to an external network, and the controllers assigned as remote controllers refuse all access requests from any external networks.

A histological sample processing procedure typically involves the use of multiple tracking stations that are associated with respective stages of the procedure, and each time a procedural step is carried out on a histological sample at a tracking station, the carrier of the histological sample may be scanned by the scanner to identify the histological sample, and a message may be sent out by the controller to the other controllers of the other tracking stations so that they are aware that the histological sample has undergone, or is currently undergoing, that procedural step.

The controller that is provided at each tracking station means that a secure network can easily be implemented between controllers, without any fear of the information that is held by the controllers being hacked or stolen via network infrastructure. This is due to the establishment of a private network wherein remote controllers refuse all access requests from other devices that do not form part of the private network. The assignment of one controller as an interface controller provides a single point of contact between the private network and an external network, for example a hospital network, to help assure the privacy of the information within the private network.

The interface controller may be a controller that is incorporated in one of the tracking stations, for example if all of the controllers of the system are incorporated in respective tracking stations. Or, the interface controller may be a controller that is not incorporated within one of the tracking stations, for example the interface controller could be implemented on a general purpose computer rather than within a tracking station.

The interface controller may be provided with a data store for storing records of histological samples, and each remote controller may be restricted to accessing the data store via the interface controller. The interface controller may restrict access of the data store to only other controllers and the external network. The data store may reside on a tracking station having the interface controller, or the data store may reside on a device forming part of the external network, and the data store may be accessible to the interface controller via the external network.

Typically, the external network is a trusted network with which the interface controller has been programmed to operate. The interface controller may refuse access to all other external networks that the interface controller has not been programmed to allow communications with.

Advantageously, the messages based on the identifiers that are sent to controllers of other ones of the tracking stations may be in the form of data bubbles, and each remote controller that receives a data bubble may forward the data bubble towards the interface controller, either directly to the interface controller, or to the interface controller via other ones of the remote controllers. Therefore, the private network may be arranged in an ad-hoc manner, without every controller requiring a direct connection to the interface controller. Clearly, if the same data bubble is received by two different remote controllers, then only one of the remote controllers is required to forward the data bubble onwards towards the interface controller.

The data bubble typically comprises an indication of the identifier that was scanned, and may comprise a timestamp indicating the time when the identifier was scanned, to help aid process scheduling and improve the flow of histological samples through the histological sample processing procedure.

Furthermore, the data bubble may comprise a request for the interface controller to supply information that is associated with the identifier from the data store. For example, the information may comprise information for printing upon a carrier of a histological sample.

Advantageously, each remote controller may be configured to read any data bubbles that it receives, in addition to forwarding the data bubbles towards the interface controller. Then, each remote controller may be kept up to date with the processing progress of the histological samples, as well as just the interface controller. Furthermore, at least one of the remote controllers may maintain a local database that is based upon the information in the data bubbles that the remote controller receives.

At least one of the tracking stations may comprise a further laboratory device that performs operations upon histological samples or carriers of histological samples. More than one further laboratory device may be included as part of each tracking station. Typically, all parts of a given tracking station are located at the same location as one another.

The further laboratory devices may include a printer, embedding centre, tissue processor, or microtome. For the avoidance of any doubt, a further laboratory device is defined as a device that performs functions upon histological samples or carriers of histological samples, and so is not a general purpose computer.

If the further laboratory device is a printer, then the printer may for example be a label printer for printing labels for application to histological sample pots, a cassette printer for printing identifiers upon cassettes, the cassettes for carrying histological samples, or a slide printer for printing identifiers upon slides, the slides for carrying slices of histological samples.

Advantageously, the controller of each tracking station may be integrated within the scanner or within a further laboratory device of the tracking station. This may remove the need for a computer to control the laboratory devices of the tracking station.

The tracking station may further comprise a colour touch panel display to provide a convenient user interface for controlling the devices of the tracking station.

The controller that is assigned as the interface controller may maintain device settings for the further laboratory device, and each controller that is assigned as a remote controller and that has a further laboratory device at its tracking station, may retrieve the device settings for the further laboratory device from the interface controller and apply the device settings to the further laboratory device. Accordingly, the updating of settings of all of the laboratory devices may be easily accomplished by just updating the settings using the interface controller, without having to manually update settings of every individual laboratory device. The interface controller may specify the device settings that are to be applied to the laboratory device based upon the type of the histological sample with which the laboratory device is about to perform a procedural step, the type of histological sample being determined based upon the message that is sent to the interface controller from the remote controller at the tracking station of the laboratory device.

The private network may be implemented over existing network infrastructure supporting existing networks, and the remote controllers may only present their network addresses to the existing networks, and no user data. Accordingly, controllers may use existing network infrastructure without any fear of other existing devices that are connected to the existing network infrastructure gaining access to the user data held by the controllers. The controllers may appear invisible to the existing network devices, except for the controllers' network addresses, for example IP addresses.

The controllers that are incorporated within the tracking stations may be pre-programmed with software and security protocols during manufacture, the software and security protocols enabling the controller to join and operate on the private network. Furthermore, the tracking stations may be configured to prevent installation of any new software for running on the controllers. For example, the tracking station may lack any possible means of loading new software into the controller, and/or the controllers may be configured to disallow installation or running of any new software beyond the pre-programmed software. Alternatively, the controllers may be configured to allow installation and running of new software, provided that the new software has been delivered to the controller via the private network, and/or provided the software comprises a security authenticator that authenticates the software as being genuine software that has been approved for use on the controller.

Advantageously, each controller may provide both wired and wireless connectivity to other controllers of the private network. This helps improve network connectivity between the controllers so that wireless communications may be attempted if a wired network connection to a given controller is not available.

Each controller may be configured to automatically detect controllers that become newly accessible via the network infrastructure, and to initiate a connection of the private network to the newly accessible controllers. Accordingly, the private network may be established autonomously without any need for a skilled network technician to set up the network. A new tracking station could be added to an existing laboratory with the controller of the new tracking station automatically detecting and connecting to existing controllers of other tracking stations.

A newly accessible controller may be assigned as a remote controller when an interface controller is already present in the private network. If an interface controller is not already present in the private network, or if the interface controller fails, then the controllers may collectively assign a new interface controller. For example, each controller may be configured to assign itself as the interface controller after a random period of time has elapsed and declare this to the network, if there is no current interface controller.

Figure 2:
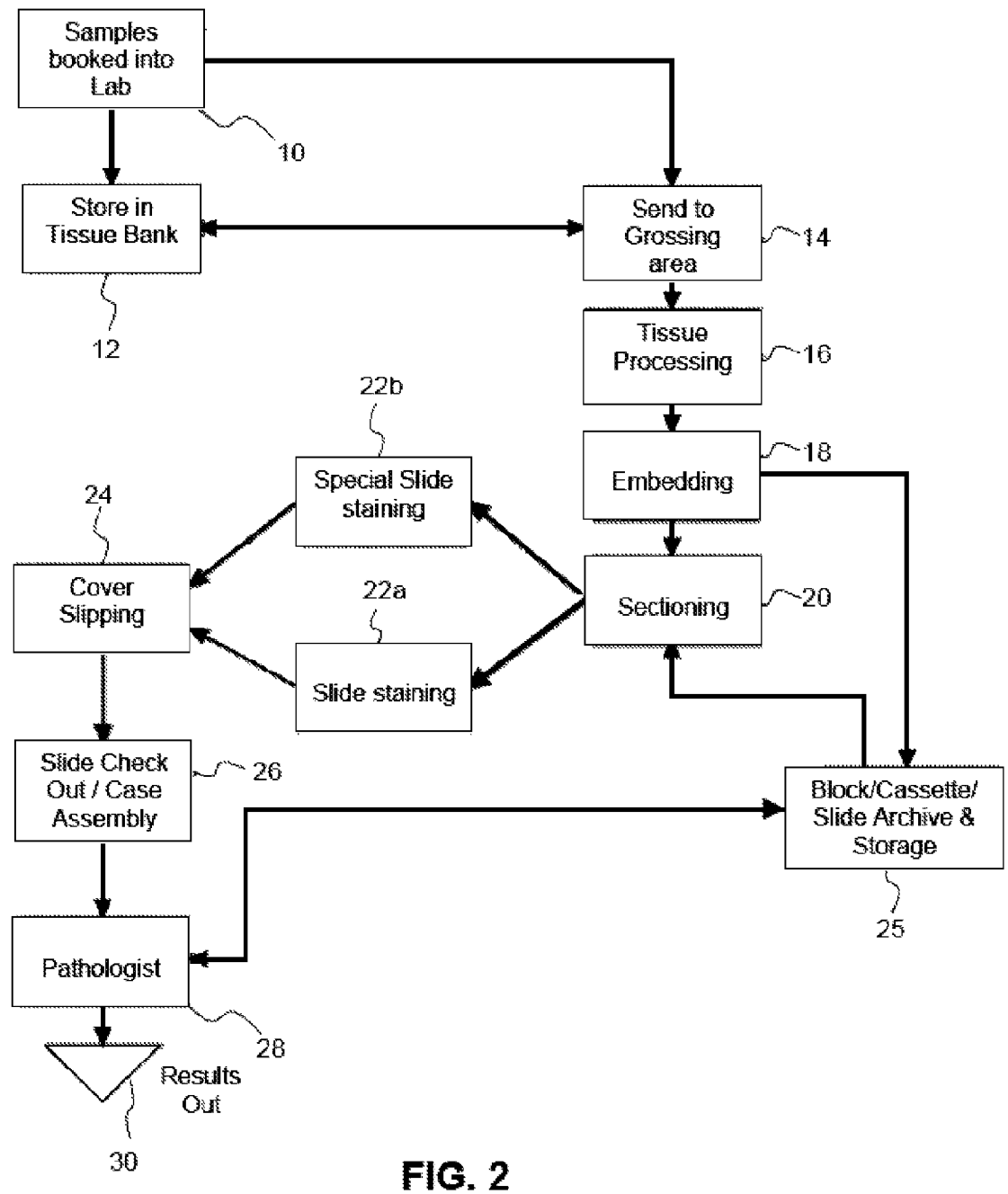
Figure 3:
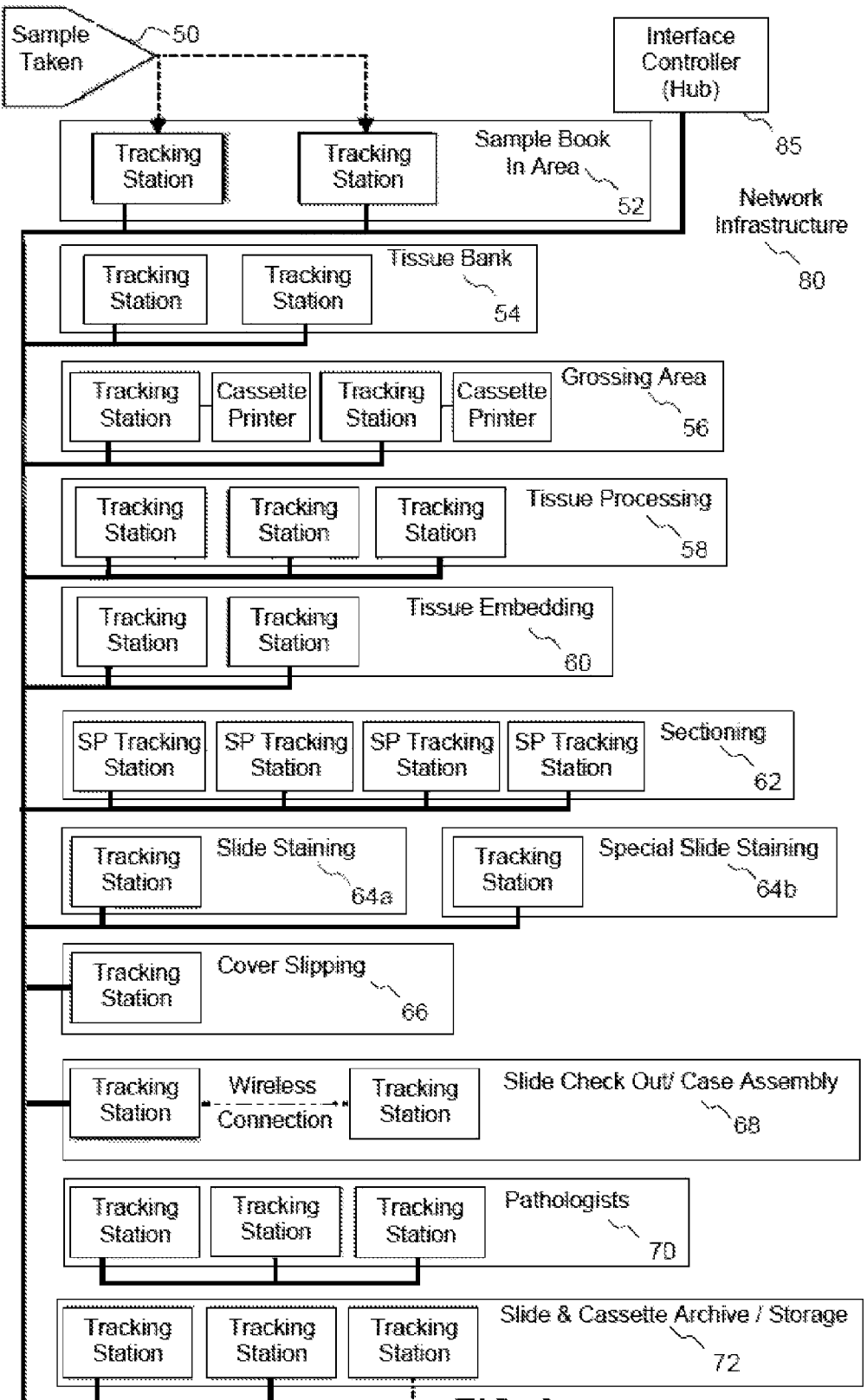

Illustrative embodiments of the invention will now be described with reference to the accompanying drawings, in which:

FIG. 1 shows a schematic diagram of a histological sample tracking system according to a first embodiment of the invention; and FIG. 2 shows a flow diagram of a histological processing method that is carried out using a histological sample tracking system according to a second illustrative embodiment of the invention; and FIG. 3 shows a schematic diagram of the histological sample tracking system of FIG. 2.

A first illustrative embodiment of the invention will now be described with reference to FIG. 1, which shows a histological sample tracking system comprising three controllers CNT_I, CNT_R1, CNT_R2, and first and second tracking stations TS1 and TS2. The controller CNT_I is assigned as an interface controller and is implemented on a general purpose computer GPC. The controllers CNT_R1, CNT_R2 are assigned as first and second remote controllers and are incorporated within the first and second tracking stations TS1 and TS2 respectively.

The controller CNT_I is programmed into the general purpose computer GPC with computer software, and can access an external network EXNT via an external network interface ENI. In this particular embodiment, the external network interface ENI is cable that is plugged into external network infrastructure. The external network interface ENI provides the interface controller CNT_I with access to a data store DS that located over the external network EXNT. The interface controller CNT_I also has the ability to access networks wirelessly, using wireless network hardware of the general purpose computer GPC. In an alternative embodiment, the data store DS is stored directly on the general purpose computer GPC, rather than on hardware that is accessed over the external network EXNT. In either case, external devices that have been authenticated on the external network can also access the data store DS, for example other general purpose computers on the external network EXNT.

The first remote controller CNT_R1 is integrated within a first scanner SCN1 of the first tracking station TS1. The first remote controller CNT_R1 is implemented as an application specific integrated circuit (ASIC) of the first scanner SCN1, and is connected to an antenna (not shown in Figs) for accessing wireless networks and a socket (not shown in Figs) for accessing wired networks.

The second remote controller CNT_R2 is integrated within a printer PRNT of the second tracking station TS2. The second remote controller CNT_R2 is implemented as a field programmable gate array (FPGA) of the printer PRNT, and is connected to an antenna (not shown in Figs) for accessing wireless networks and a socket (not shown in Figs) for accessing wired networks. The second tracking station TS2 also incorporates a second scanner SCN2, which is connected to the printer PRNT.

Upon powering up the histological sample tracking system, the controller CNT_I joins the external network EXNT, and then assigns itself as an interface controller. The interface controller CNT_I then creates a private network, and advertises the existence of the private network using its wired and wireless network connections.

The controllers CNT_R1 and CNT_R2 search for the private network using their wired and wireless network connections, however, in this embodiment, the controllers CNT_R1 and CNT_R2 are not connected to any wired networks, and so do not discover any networks via their network sockets.

The controller CNT_R1 discovers the private network through its wireless network connection (antenna). The controller CNT_R1 has been pre-programmed with security protocols so that it can authenticate itself to the controller CNT_I as a genuine controller, and so joins the private network by establishing a wireless private network connection PNC1 with the controller CNT_I. The controller CNT_R1 recognises that the private network already has an interface controller CNT_I, and so assigns itself as a remote controller. The remote controller CNT_R1 declares to the private network that it is located at the first tracking station TS1. Once the controller CNT_R1 has assigned itself as a remote controller on the private network, it refuses all access requests from any other networks, including the external network.

The controller CNT_R2 is too physically far away from the interface controller CNT_I to properly receive wireless signals sent by the interface controller CNT_I. However, the controller CNT_R2 is within wireless range of the first remote controller CNT_R1. The controller CNT_2 detects the presence of the first remote controller CNT_R1, and authenticates itself to the first remote controller CNT_R1 as a genuine controller. The first remote controller CNT_R1 informs the controller CNT_R2 that a private network having the interface controller CNT_I has already been established, and, then, the controller CNT_R2 joins the private network via a wireless private network connection PNC2 that is established with the controller CNT_R1. Since the private network already has an interface controller CNT_I, the controller CNT_R2 assigns itself as a (second) remote controller and refuses all access requests from any other networks, including the external network. The remote controller CNT_R2 declares to the private network that it is located at the second tracking station TS2.

In this embodiment, the external network EXNT is a hospital network, and the general purpose computer GPC and first and second tracking stations TS1 and TS2 are within a laboratory. The use of the histological sample tracking system of FIG. 1 to track histological samples will now be described.

Histological samples are taken from patients, placed in histological sample pots having individual bar codes, and sent to the laboratory for analysis. Upon arrival of a histological sample pot at the laboratory, the bar code of the histological sample pot is scanned by the first scanner SCN1 of the first tracking station TS1, to book the histological sample into the laboratory.

Specifically, the scanned bar code is received by the first remote controller CNT_R1, and the first remote controller sends a first data bubble to the private network. The first data bubble includes the scanned bar code, a destination address corresponding to the interface controller CNT_I, and an origination address corresponding to the first remote controller CNT_R1. The first data bubble is transmitted directly to the interface controller CNT_I via the private network connection PNC1.

In response to receiving the first data bubble, the interface controller CNT_I accesses the data store DS over the external network EXNT and updates the data store DS to indicate that the histological sample corresponding to the scanned barcode in the data bubble has arrived at the laboratory for processing. In this embodiment, an entry corresponding to the scanned bar code already existed in the data store DS, from when the histological sample was first taken from the patient and placed in the histological sample pot.

Optionally, the existing entry in the data store DS may only designate a particular person from which the sample originated, and a label printer could also be incorporated into the first tracking station TS1 for printing a bar code on a label for application to the histological sample pot. The bar code on the label would designate that the histological sample pot held a particular histological sample of the particular person.

The histological sample in the sample pot typically needs to be split into smaller samples for ease of subsequent processing, and/or so that multiple tests can be run on the histological sample. This splitting of the histological sample into smaller samples is commonly referred to as a grossing process, and the smaller samples are placed into respective containers commonly referred to as cassettes.

When the histological sample is to undergo the grossing process, the histological sample pot is taken to the second tracking station TS2, and the bar code of the histological sample pot is scanned by the second scanner SCN2. The scanned bar code is received by the second remote controller CNT_R2, and the second remote controller sends a second data bubble to the private network.

The second data bubble includes the scanned bar code, a destination address corresponding to the interface controller CNT_I, and an origination address corresponding to the second remote controller CNT_R2. Since the second remote controller CNT_R2 does not have a direct link to the interface controller CNT_I, the second data bubble is transmitted to the first remote controller CNT_R1 via the private network connection PNC2, and the first remote controller CNT_R1 reads the destination address of the second data bubble and so forwards the second data bubble onto the interface controller CNT_I via the private network connection PNC1.

In response to receiving the second data bubble, the interface controller CNT_I accesses the data store DS over the external network EXNT and updates the data store DS to indicate that the histological sample corresponding to the scanned barcode in the second data bubble has arrived at the second tracking station for grossing. The interface controller CNT_I knows that the histological sample corresponding to the scanned barcode in the second data bubble has arrived at the second tracking station for grossing, because the origination address of the second data bubble corresponds to the second remote controller CNT_R2, and the second remote controller CNT_R2 declared to the private network that it was located at the second tracking station (grossing station) TS2 when the second remote controller CNT_R2 first joined the private network.

Since the histological sample has arrived at the second tracking station, and is therefore about to be grossed into smaller samples that are placed in respective cassettes, the interface controller CNT_I sends a third data bubble to the second remote controller CNT_R2 that includes a number of barcodes which are to be applied to the respective cassettes. Alternatively, the second remote controller CNT_R2 sends a request to the interface controller CNT_I for such a third data bubble to be sent to it, and the request may be included in the second data bubble described above.

The second remote controller CNT_R2 receives the third data bubble, and instructs the printer PRNT to print the bar codes specified in the third data bubble onto the respective cassettes. In this embodiment, the third data bubble also includes printer settings that instruct the printer PRNT on how the bar codes should be printed, the printer settings corresponding to standardised print settings that are stored in the data store DS. The printer PRNT is a cassette printer, which is specifically designed to print upon cassettes.

Once the printer PRNT has completed printing of the bar codes onto the cassettes, the second remote controller CNT_R2 sends a fourth data bubble to the interface controller CNT_I that indicates that the printing has been completed, and the interface controller CNT_I updates the data store DS accordingly.

The data bubbles described above all include the destination and origination addresses of the controllers to which they are destined and to which they originate from, and the data bubbles travelling between the interface controller and the second remote controller must pass via the first remote controller as there is no direct connection between the interface controller and the second remote controller. Therefore, the first remote controller can read all of the data bubbles passing between the interface controller and the second remote controller, and may maintain a local database of the data bubbles so the first remote controller CNT_R1 can keep track of the processing status of the histological sample.

In an alternative embodiment, the interface controller CNT_I and the second remote controller CNT_R2 do have a direct connection between them, for example a wired network connection, and so the data bubbles can be sent over the private network directly via the wired network connection without needing to be transmitted via the first remote controller CNT_R1.

If the interface controller CNT_I was to become inoperative, for example through failure of the general purpose computer GPC, then the first and second remote controllers recognise that the interface controller is no longer part of the private network, and that the private network lacks an interface controller and a connection to the external network. Each remote controller waits for a random period of time, and if an interface controller is still not present on the private network, then the remote controller assigns itself as the interface controller and attempts to connect to the external network. If the connection to the external network is not successful, then the controller reassigns itself as a remote controller.

A second illustrative embodiment of the invention will now be described, in relation to FIG. 2 which shows a flow diagram of a histological sample processing method, and in relation to FIG. 3 which shows one way in which tracking stations that are used to implement the FIG. 2 histological sample processing method could be arranged.

A histological sample is taken from a patient in a room 50, for example within a hospital, and placed within a histological sample pot. The histological sample pot is then taken to a laboratory for processing, and the histological sample processing method comprises a step 10 of booking the newly received histological sample pot into the laboratory at a Booking In Area 52, by scanning a bar code on the sample pot using one of the tracking stations at the Booking In Area 52. The controller of the tracking station creates a transaction with a digital signature for the scanned bar code, and sends the data in a data bubble to an interface controller 85 via a network infrastructure 80. The interface controller 85 may be defined by an application running on a PC, or may be a designated tracking station.

The network infrastructure 80 is an existing wired network infrastructure, which the controllers of the tracking stations and the interface controller use to implement the private network. The interface controller 85 may also be referred to as a hub of the private network, since it (and it alone) forms a connection between the private network and an external network. The interface controller 85 comprises a data store which is used to store data for tracking histological samples.

The histological sample in the sample pot is either placed in temporary storage for a step 12, the Tissue Bank 54, or is sent direct to a Grossing area 56 for a step 14, where the histological sample.

The tissue bank 54 includes two tracking stations for booking histological samples in and out of the tissue bank. The tracking stations send data bubbles to the interface controller 85, via the private network on the network infrastructure 80, so that the interface controller 85 can update its data store to log that the histological sample has just been booked into or out of the tissue bank 54. The data bubbles preferably include an indicator specifying whereabouts in the tissue storage bank the histological sample is stored.

The grossing area 56 also includes two tracking stations that each have a cassette printer for printing barcodes onto cassettes. At Grossing the histological sample is divided up and placed into cassettes. The barcode on the histological sample pot is scanned, and sent to the interface controller within a data bubble, and the interface controller returns a data bubble to the tracking station that instructs the cassette printer to print bar codes onto cassettes. The divided up histological samples are placed within the cassettes, and these cassettes are placed into racks for subsequent Tissue Processing.

After Grossing, the racks are taken to a Tissue Processing area 58 for a Tissue Processing step 16, which prepares the histological sample for subsequent processing steps, and can take a few hours to complete. The racks or the cassettes can be scanned at a tracking station upon arrival at the Tissue Processing area 58 to send a data bubble to the interface controller that indicates the cassettes have reached Tissue Processing.

After Tissue Processing, the racks containing the cassettes are taken to a Tissue Embedding area 60 for an Embedding step 18. The cassettes are removed individually from the rack, and scanned by a tracking station at the Tissue Embedding area 60 to send a data bubble to the interface controller that indicates the cassettes have reached the Tissue Embedding area 60, and that requests embedding instructions. The interface controller responds by sending a data bubble back to the tracking station that includes embedding instructions for how the histological sample in the cassette is to be embedded, for example the temperatures required for the embedding process. The step 18 of embedding takes the histological sample from the cassette, and places it in a wax block on the back of the cassette. The cassette is then cooled and sent to a Sectioning area 62 for a Sectioning step 20.

Upon arrival at the Sectioning area 62, the cassette with the wax block is scanned by a slide printer tracking station with an integral controller, and the scanned data is used to populate slide data fields for printing on slides. In particular, the slide printer tracking station creates a transaction with a digital signature for the scanned cassette, and sends the data in a data bubble to the interface controller 85 via the network 80. The interface controller checks the data store for any related data such as slides that have been pre-ordered. If there are any pre-ordered slides, then the interface controller sends a data bubble to the slide printer tracking station that includes information on the pre-ordered slides for printing. The Sectioning slices the histological sample into thin slices, which are then placed on the slides. Each slide printer tracking station is labeled "SP Tracking Station" in FIG. 3.

The cassettes or slides may be stored or archived 25 after the Embedding or Sectioning steps in a storage or archive area 72, for example so that they can be inspected by a pathologist whilst awaiting the next step in their processing. As they are placed into storage, they are scanned by a tracking station and their storage locations added. The tracking stations create transactions with digital signatures for the scanned items and send the data in a data bubble to the interface controller via the network.

After the Sectioning step 20, the slides are stained in a step 22a at an area 64a. The slides are scanned by a tracking station at the area 64a as they are stained, or as the stained slides are placed into racks. The tracking stations create transactions with digital signatures for scanned items and send the data in a data bubble to the interface controller via the network.

After staining, the slides are moved to an area 66 for a Cover Slipping step 24. The slides are scanned by a tracking station at the area 66 as they are cover slipped, or as the cover slipped slides are placed into racks. The tracking stations create transactions with digital signatures for scanned items and send the data in a data bubble to the interface controller via the network.

After cover slipping and drying, the slides are assembled into cases in a step 26 at an area 68. The slides are scanned by a tracking station at the area 68, and the tracking stations create transactions with digital signatures for scanned items, and send the data in a data bubble to the interface controller via the network. The Interface controller sends the tracking station all related data so the tracking station can verify that the slide is in the correct group. All errors are recorded and transactions created with digital signatures. One of the tracking stations at area 68 does not have a direct link to the network infrastructure 80, and so establishes a wireless link with a tracking station that is connected to the network infrastructure 80, in order to join the private network.

Once the slides have been grouped they are given to the Pathologist to review in a step 28 at an area 70. As the Pathologist reviews the slides, they are scanned by a tracking station at the area 70. The tracking station creates transactions with digital signatures for the scanned items, and sends the data in a data bubble to the interface controller via the network. The Pathologist may order additional slides to be retrieved from the storage or archive area 72, and for the slides to be stained with special stains in a step 22b at area 64b. The final results determined by the pathologist are output in a final step 30 of the method.

All of the scanned data and user actions during the above histological processing method are recorded and stored in the data store of the interface controller 85, and can be retrieved by the tracking stations as required.

For example, a user could scan a slide at a tracking station and retrieve all related data such as the parent cassette and other related printed or ordered slides.

Many other embodiments falling within the scope of the appended claims will also be apparent to those skilled in the art. For example, although the sample pots/cassettes/slides are tracked using bar code identifiers in the above embodiments, other types of identifier could alternatively be used, for example QR codes, or electronic code carriers such as RFID tags.

The invention claimed is:

1. A histological sample tracking system, comprising a plurality of tracking stations and controllers, each tracking station incorporating a scanner and one of the controllers, wherein the scanner is configured to scan identifiers of carriers of histological samples and wherein the controller is configured to receive the identifiers and send messages based on the identifiers, the controllers together forming a private network, wherein one of the controllers is assigned as an interface controller and the remaining controllers are assigned as remote controllers, wherein the controller assigned as the interface controller allows access to an external network, wherein the messages based on the identifiers are sent to other ones of the controllers of the tracking stations, each tracking station being associated with a respective stage of a historical sample processing procedure, and wherein the controllers assigned as remote controllers refuse all access requests from any external networks.

2. The histological sample tracking system of claim 1, wherein the interface controller is provided with a data store for storing records of histological samples, and wherein each remote controller is restricted to accessing the data store via the interface controller.

3. The histological sample tracking system of claim 1, wherein the messages based on the identifiers that are sent to controllers of other ones of the tracking stations are in the form of data bubbles, and wherein each remote controller that receives a data bubble forwards the data bubble towards the interface controller, either directly to the interface controller, or to the interface controller via other ones of the remote controllers.

4. The histological sample tracking system of claim 3, wherein the data bubble comprises a request for the interface controller to supply information associated with the identifier from the data store.

5. The histological sample tracking system of claim 4, wherein the information comprises information for printing upon a carrier of a histological sample.

6. The histological sample tracking system of claim 3, wherein each remote controller is configured to read any data bubbles received, in addition to forwarding the data bubbles towards the interface controller.

7. The histological sample tracking system of claim 6, wherein at least one of the remote controllers maintains a local database that is based upon the information in the data bubbles that the remote controller receives.

8. The histological sample tracking system of claim 1, wherein at least one of the tracking stations comprises a further laboratory device that performs operations upon histological samples or carriers of histological samples.

9. The histological sample tracking system of claim 8, wherein the controller that is assigned as the interface controller maintains device settings for the further laboratory device, and wherein each controller that is assigned as a remote controller and that has a further laboratory device at the remote controller's tracking station, retrieves the device settings for the further laboratory device from the interface controller and applies the device settings to the further laboratory device.

10. The histological sample tracking system of claim 8, wherein at least one of the tracking stations comprises the further laboratory device in the form of a label printer for printing labels for application to histological sample pots.

11. The histological sample tracking system of claim 8, wherein at least one of the tracking stations comprises the further laboratory device in the form of a cassette printer for printing identifiers upon cassettes, the cassettes for carrying histological samples.

12. The histological sample tracking system of claim 8, wherein at least one of the tracking stations comprises the further laboratory device in the form of a slide printer for printing identifiers upon slides, the slides for carrying slices of histological samples.

13. The histological sample tracking system of claim 8, wherein the controller of each tracking station is integrated within the scanner or within the further laboratory device of the tracking station.

14. The histological sample tracking system of claim 1, wherein the private network is implemented over existing network infrastructure supporting existing networks, and wherein the remote controllers only present their network addresses to the existing networks, and no user data.

15. The histological sample tracking system of claim 1, wherein each controller offers both wired and wireless connectivity to other controllers of the private network.

16. The histological sample tracking system of claim 1, wherein each controller is configured to automatically detect controllers that become newly accessible via network infrastructure, and to initiate a connection of the private network to the newly accessible controllers.

17. The histological sample tracking system of claim 16, wherein the newly accessible controllers are assigned as remote controllers when an interface controller is already present in the private network.

18. The histological sample tracking system of claim 2, wherein the data store resides on the tracking station having the interface controller.

19. The histological sample tracking system of claim 2, wherein the data store resides on a device forming part of the external network, and wherein the data store is accessible to the interface controller via the external network.

20. The histological sample tracking system of claim 1, wherein the interface controller does not form part of any of the tracking stations.

* * * * *